United States Patent [19]

Botta et al.

[11] Patent Number: 5,053,566
[45] Date of Patent: Oct. 1, 1991

[54] PROCESS FOR THE PREPARATION OF OLIGOPHENYLS DIHALOGENATED IN THE 4,4'-POSITION

[75] Inventors: Artur Botta; Hans-Josef Buysch, both of Krefeld; Lothar Puppe, Burscheid, all of Fed. Rep. of Germany

[73] Assignee: Bayer Aktiengesellschaft, Leverkusen, Fed. Rep. of Germany

[21] Appl. No.: 571,956

[22] Filed: Aug. 23, 1990

[30] Foreign Application Priority Data

Sep. 15, 1989 [DE] Fed. Rep. of Germany ....... 3930848

[51] Int. Cl.$^5$ .................. C07C 17/12; C07C 25/18
[52] U.S. Cl. ................................. 570/208; 570/206; 570/207
[58] Field of Search ................. 570/206, 207, 208

[56] References Cited

U.S. PATENT DOCUMENTS

| | | | |
|---|---|---|---|
| 3,833,674 | 9/1974 | Brackenridge | 570/208 |
| 4,950,817 | 8/1990 | Botta | 570/208 |

FOREIGN PATENT DOCUMENTS

| | | | |
|---|---|---|---|
| 0154236 | 9/1985 | European Pat. Off. | 570/208 |
| 0231662 | 8/1987 | European Pat. Off. | 570/208 |
| 0334097 | 9/1989 | European Pat. Off. | 570/208 |
| 0349381 | 1/1990 | European Pat. Off. | |
| 2056441 | 5/1971 | Fed. Rep. of Germany | |
| 2155009 | 9/1985 | United Kingdom | |

OTHER PUBLICATIONS

Synthesis No. 12, Dec. 1985, pp. 1157, 1158, Stuttgart, Del.; K. Smith: "Highly Para-Selective Mono-Chlorination of Aromatic Compounds Under Mild Conditions by t-Butyl Hypochlorite in the Presence of Zeolites". Patent Abstracts of Japan, vol. 4, No. 101 (C-19) (593), Jul. 19, 1980; & JP-A-5564532 (Hodogaya Kagaku) May 15, 1980.

*Primary Examiner*—Werren B. Lone

*Attorney, Agent, or Firm*—Sprung Horn Kramer & Woods

[57] ABSTRACT

Oligophenyls dihalogenated in the 4,4'-position, of the formula

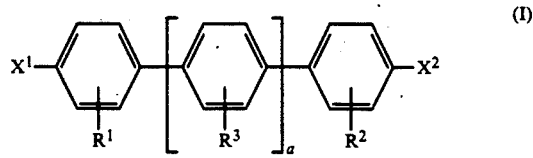

(I)

can be prepared by catalyzed halogenation of oligophenyls of the formula

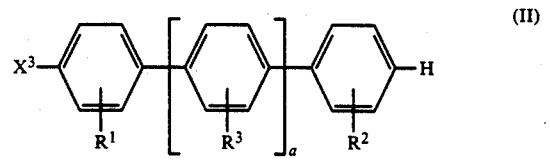

(II)

wherein, in the formulae,
- $X^1$ and $X^2$ independently of one another represent chlorine or bromine, preferably chlorine,
- $X^3$ denotes hydrogen, chlorine or bromine, preferably hydrogen or chlorine and particularly preferably hydrogen,
- $R^1$, $R^2$ and $R^3$ independently of one another represent hydrogen, $C_1$-$C_4$-alkyl (preferably methyl or ethyl and particularly preferably methyl), $C_1$-$C_4$-alkoxy (preferably methoxy or ethoxy and particularly preferably methoxy), fluorine, chlorine or bromine and
- a assumes the value zero or one, with halogenating agents, the preparation being carried out in the presence of methylene chloride or solvent mixtures essentially containing methylene chloride and in the presence of zeolites of the L structure type which contain metal cations.

18 Claims, No Drawings

PROCESS FOR THE PREPARATION OF OLIGOPHENYLS DIHALOGENATED IN THE 4,4'-POSITION

BACKGROUND OF THE INVENTION

1. Field of the Invention

The invention relates to a process for the selective halogenation of oligophenyls in the 4,4'-position in the presence of zeolites having pore widths of at least 5 Å and also in the presence of methylene chloride.

Oligophenyls which are halogenated in the p-position on both sides, such as 4,4'-dichloro- and 4,4'-dibromodiphenyl or -terphenyl, are claiming great industrial interest, for example as intermediate products for plastics of high heat resistance, such as polyphenylene sulphide (compare Japanese Patent Application 61/231,030 and U.S. Pat. No. 3,396,110 [C.A. 69, P 60 564 w]).

2. Description of the Related Art

Conventional chlorination of diphenyl in the presence of Lewis acids leads to non-selective random substitution, the 4,4'-derivative not being the preferred derivative. Chlorination at 100° C. in the presence of 2.5% by weight of $FeCl_3$ thus produces a selectivity of only 8% for the 4,4'-dichloro isomer; the content of trichlorobiphenyl is remarkably high, at 15%, polychlorinated biphenyls, as is known, belonging to highly toxic classes of substances. According to the information in U.S. Pat. No. 1,946,040, U.S. Pat. No. 3,226,447 and British Patent Specification 1,153,746, the addition of a sulphur compound during the chlorination of benzenes is said to increase the selectivity in favour of para-substitution. As the comparison example described below shows, however, in such a chlorination of biphenyl by addition of 2.5% by weight of thiophene, in addition to 2.5% by weight of $FeCl_3$, the selectivity is increased only insignificantly in favour of 4,4'-dichlorobiphenyl, whereas polychlorinated biphenyls still make up a considerable proportion of the reaction product, at more than 9% by weight. This fact indicates that biphenyl and benzene are comparable to only a very limited degree.

The chlorination of p-terphenyl in the presence of iron and chloroform leads to a random mixture of o-and p-monochloro- and o,p'- and p,p'-dichloro-terphenyls, which could be separated only with great technical expenditure because of the sparingly soluble nature of the p-isomers (Bull. Soc. Chim. France 1968 (10), 4255–58 [C.A. 70 (1969), 57 316 g]).

The use of Lewis acids in practice furthermore as is known leads to increased corrosion problems and to a more difficult working up and disposal.

SUMMARY OF THE INVENTION

A process has now been found for the preparation of oligophenyls dihalogenated in the 4,4'-position, of the formula

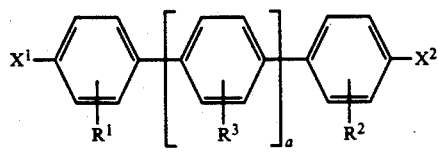

(I)

by catalysed halogenation of oligophenyls of the formula

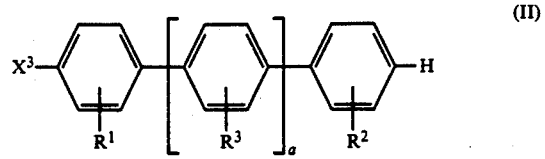

(II)

wherein, in the formulae,
$X^1$ and $X^2$ independently of one another represent chlorine or bromine, preferably chlorine,
$X^3$ denotes hydrogen, chlorine or bromine, preferably hydrogen or chlorine and particularly preferably hydrogen,
$R^1$, $R^2$ independently of one another represent and $R^3$ hydrogen, $C_1$–$C_4$-alkyl (preferably methyl or ethyl and particularly preferably methyl), $C_1$–$C_4$-alkoxy (preferably methoxy or ethoxy and particularly preferably methoxy), fluorine, chlorine or bromine and
a assumes the value zero or one,
with halogenating agents, which is characterized in that the process is carried out in the presence of methylene chloride or solvent mixtures essentially containing methylene chloride and in the presence of zeolites of the L structure type containing metal cations.

DETAILED DESCRIPTION OF THE INVENTION $C_1$–$C_4$-Alkyl is, for example, methyl, ethyl, propyl, isopropyl, butyl, isobutyl or tert.-butyl.

$C_1$–$C_4$-Alkoxy is, for example, methoxy, ethoxy, propoxy, isopropoxy, butoxy, isobutoxy or tert.-butoxy.

In the case where the index a assumes the value zero, the invention relates to the dihalogenation of biphenyl. In the case where the index a assumes the value one, the invention relates to the dihalogenation of terphenyls in which the three phenyl nuclei are linked linearly. The halogenation of the oligophenyls substitutes, according to the invention, the p-position to the ring linkage with exceptionally high selectivity.

As 4,4'-dihalogenation, the invention relates to chlorination and bromination, but preferably chlorination. Starting materials which can be employed are the biphenyls or terphenyls which are not yet halogenated in the 4- and 4'-position; however, in the context of the definition for $X^3$, it is also possible for biphenyls or terphenyls which are already monohalogenated in the p-position to be reacted according to the invention. This is of importance on the one hand for the recycling of monohalogenation product obtained in the process according to the invention, but on the other hand for the fact that according to the invention it is possible to prepare 4,4'-dihalogenated biphenyls or terphenyls in which $X^1$ and $X^2$ represent different halogen atoms if a monochloro-or monobromo-oligophenyl is employed and the process is carried out according to the invention with a brominating agent or a chlorinating agent to introduce the other respective halogen. The halogenation of the oligophenyls is preferably halogenation of unsubstituted biphenyl or unsubstituted, linearly linked terphenyl.

Suitable halogenating agents are chlorine or bromine, as well as compounds which liberate chlorine or bromine, such ⁓s sulphuryl chloride, sulphuryl bromide, N-chloro- and N-bromosuccinimide and also bromine chloride, bromine fluoride and other halogenating agents of this type which are known to the expert. Elemental chlorine or elemental bromine is preferably employed. Chlorination with the aid of elemental chlorine is particularly preferred. The halogenating agent is as a rule employed in a stoichiometric ratio to the oligophenyl, that is to say in a molar ratio of 2:1 in the case of oligophenyls which are not yet halogenated in the 4- and 4'-position, and in a molar ratio of 1:1 in the case of oligophenyls which are already monohalogenated in the 4-position. This stoichiometric ratio can be deviated from upwards by up to 60 mol %, preferably up to 40 mol % and particularly preferably up to 30 mol %, or downwards by up to 20 mol %.

The process according to the invention is carried out in the presence of zeolites of the L structure type, in which at least some of all the replaceable cations are metal cations. Zeolites are crystalline alumosilicates which are built up from a network of $SiO_4$ and $AlO_4$ tetrahedra. The individual tetrahedra are linked to one another at the corners via oxygen bridges and form a spatial network through which channels and hollow spaces run. Replaceable cations are intercalated to compensate for the negative charge of the frame work.

These types of zeolites can be provided with replaceable cations from their synthesis form or any large number of other cations in the sense of ion exchange. This exchange is prior art and certainly known to the expert. Si and Al in the zeolites can be replaced at least partly by other elements. A detailed description of zeolites is given, for example, in the monograph by D. W. Breck "Zeolite Molecular Sieves, Structure, Chemistry, and Use", J. Wiley and Sons, New York, 1974.

The zeolite L structure type can contain as cations, for example, those of Li, Na, K, Rb, Cs, Ca, Mg, Sr and Ba, of rare earth metals, such as La and Ce, and of other metals, such as Fe, Zn, Mn, Cr, Co, Ni, Ti, Cu, Ag and Pb, or mixtures of these, preferably cations of K, Rb, Cs, Ca, Sr, Ba, Ag, Pb and La or mixtures of these. A zeolite L in which 60–100 equivalent %, preferably 80–100 equivalent % and particularly preferably 90–100 equivalent % of all cations are metal cations is possible for the use according to the invention.

The zeolite is employed in an amount of 1–100% by weight, preferably 3–50% by weight and particularly preferably 5–30% by weight, based on the weight of oligophenyl to be reacted.

The shape of the employed zeolite catalyst is not critical for the process according to the invention, in general. As a rule, especially in a batch variant, the catalyst can be used as a powder. Of course, it is also possible (e.g. in a continuous reaction in the gas, liquid or trickle phase, wherein the catalyst is arranged as a fixed bed) to use the catalyst in pieces or in granulated form to yield a better separation from the reaction product. Herewith usual binding and forming auxiliary agents which are known to the skilled artisan may be co-used which are inert towards the halogenating agents, e.g. $SiO_2$, $Al_2O_3$, argillaceous earth, graphite etc. in an amount of 0.1–80%, preferably 2–30% by weight, relative to the amount of the pure zeolite.

The process according to the invention is characterized in particular by the fact that it is carried out in the presence of methylene chloride or mixtures essentially containing methylene chloride. In fact, it has been found, surprisingly, that if the process is carried out in the presence of methylene chloride, selectivities of oligophenyl of the formula (I) dihalogenated in the 4,4'-position of at least 90% are achieved, which are not achieved with other compounds which are closely related to methylene chloride, such as chloroform or carbon tetrachloride, or with other compounds used as solvents. The high selectivity is all the more surprising since the use of methylene chloride in the process according to the invention is already effective in amounts which are not sufficient to dissolve completely the oligophenyl employed which is to be halogenated, and are even less sufficient to dissolve completely the dihalogenation product, which is as a rule more sparingly soluble. The amount of methylene chloride employed is accordingly 0.3–100 times, preferably 0.5–50 times and particularly preferably 1–20 times the weight of oligophenyl employed. The lower limit of the stated range of amounts is determined above all by the technological measure that the heterogeneous mixture of zeolite/starting material/methylene chloride is still stirrable. In the upper region of the stated range of amounts, conditions are achieved under which the starting material is dissolved completely, but the dichlorinated end product is no longer completely dissolved and represents a second solid disperse phase alongside the zeolite.

In addition to the methylene chloride, other liquid compounds which are known as solvents for chlorination reactions can be co-used. Examples of these are hydrocarbons or halogenohydrocarbons, such as petroleum ether, chloroform, carbon tetrachloride, 1,1,1-trichloroethane, 1,2-dichloroethane, 1,2-dibromopropane, perchloroethane, perchloroethylene, lower carboxylic acids, such as acetic acid, and other solvents known to the expert. However, the methylene chloride is always present as the essential constituent of a mixture of methylene chloride/other solvent, for example in an amount of 50–100% by weight, preferably 75–100% by weight of such a mixture. Methylene chloride is particularly preferably used by itself.

Substances known as cocatalysts for chlorination, for example from the series of lower alcohols, lower carboxylic acids, sulphur compounds and/or quaternary ammonium salts, can be co-used in the process according to the invention, but in general do not provide further advantages, so that their co-use is preferably dispensed with.

In the case where they are co-used, an amount of 0.02–20% by weight, preferably 0.02–2% by weight, based on the amount of zeolite catalyst, may be mentioned.

The reaction temperature is in general in the range from 0° C. to +80° C. The pressure is not critical for the process according to the invention and serves merely to establish the desired reaction temperature. Thus, for example, in the upper region of the temperature range mentioned the reaction is carried out under increased pressure, for example the endogenous pressure established in the system. The procedure under atmospheric pressure at 10°–45° C. is preferred.

The process according to the invention is accordingly characterized in that, because of the presence of the methylene chloride, a liquid reaction medium is present, in which the zeolite catalyst is suspended and in which the oligophenyl to be reacted is dissolved or partly likewise suspended. The fact that the process according to the invention can also be carried out equally successfully using a partly suspended starting material can be utilized to achieve a higher space-time yield. Such a procedure, in which some of the starting substance and above all the more sparingly soluble process product are also suspended, in addition to the zeolite catalyst, is therefore preferred. According to this last-mentioned process variant, the process according to the invention is carried out, for example, by a procedure in which the oligophenyl is suspended in the methylene chloride (if appropriate co-using the abovementioned solvents), while stirring. The zeolite catalyst is then added in powdered or granulated form, and 2 mol of the halogenating agent are then passed into the liquid-disperse phase at the reaction temperature at the rate at which the halogenating agent is consumed.

This variant of the halogenation process according to the invention accordingly allows substance conversions from a starting material which is largely undissolved in the reaction medium into a reaction product which is likewise largely undissolved, the halogenation proceeding at a high speed in the case of a procedure under atmospheric pressure at mild temperatures. The specific material characteristic of methylene chloride is evidently of critical importance for the transportation processes into and out of the pore and channel system of the zeolite, which is likewise insoluble in the reaction medium of methylene chloride, and for the catalytic form/selective action of the catalyst. In spite of the presence of several disperse phases, no blockage or deactivation phenomena occur in the zeolite catalyst.

In a continuous variant of the process according to the invention column apparatus, as an example, are suitable in which the zeolite catalyst is arranged on different trays in pieces or in granulated from or as a powder. Over such an arrangement the oligophenyl/-methylene chloride mixture and the halogenating agent are carried concurrently or countercurrently. Practically, in this case such a dilution with the methylene chloride is chosen that not only the educt oligophenyl, but also the product 4,4'-dihalogeno-oligophenyl remain dissolved.

For working up of the reaction mixture in which the zeolite catalyst and the 4,4'-dihalogeno-oligophenyl are present as different disperse solid phases, the dihalogeno-oligophenyl is extracted from the zeolite. For such an extraction the zeolite catalyst can be extracted with a suitable solvent, in particular while hot. Examples of solvents for this are: aliphatic or aromatic hydrocarbons, such as ligroin, cyclohexane, toluene, xylene, chlorobenzene or o-dichlorobenzene; esters, such as butyl acetate or methylglycol acetate, or amides, such as dimethylformamide.

In principle, an additional larger amount of methylene chloride is also suitable for this, this solvent being employed exclusively for its property as an extraction agent during this working up. It is furthermore possible in principle for the zeolite catalyst also to be leached out by a suitable amount of a suitable solvent without using higher temperatures. Yet another variant, which at the same time is a preferred variant, comprises extracting the finished reaction mixture with the methylene chloride present in the reaction mixture in a suitable pressure apparatus by using higher temperatures. Because of the increased dissolving capacity of the methylene chloride for the 4,4'-dihalogeno-oligophenyl at a higher temperature, for example at 80°-100° C., separation from the zeolite is achieved. Pressure filtration then follows, the pressure and temperature being maintained. After cooling, the desired reaction product separates out of the filtrate. It may be advantageous for the reaction apparatus to be equipped with a device for pressure filtration, so that the halogenation according to the invention, the extraction just described and the associated pressure filtration can be performed in one apparatus.

In case of a continuous method of working with the 4,4'-dihalogeno-oligophenyl resulting in dissolved form, it is recovered by filtration, optionally under subatmospheric pressure, and concentrating the filtrate.

Since as a rule the desired 4,4'- or 4,4"-dihalogeno-oligophenyl has a significantly lower solubility compared with any halogenated oligophenyls of different substitution pattern also formed, the dihalogeno-oligophenyl obtained from the reaction or extraction medium by crystallization has a high purity of almost 100%. Recrystallization, for example from toluene or o-dichlorobenzene, is possible for further increasing the purity.

Starting materials which have not reacted or have not reacted completely can be recycled. The zeolite catalyst which remains as the extraction residue can in general be employed again according to the invention without further activation. If a reduction in activity is found after the zeolite catalyst has been re-used several times, it can be reactivated by a customary process, for example by calcining at elevated temperature (400°-600° C.).

The yields/selectivities for the desired 4,4'-dihalogeno-oligophenyls are at least 90%, and as a rule considerably above 90%. For example, a selectivity of 96-97% is achieved both in the case of 4,4'-dichlorobiphenyl and in the case of 4,4"-dichloro-para-terphenyl. Such high selectivities were not to be expected from knowledge of the prior art. Although para-monochlorination of benzenes substituted by chlorine, lower alkyl or lower alkoxy in the presence of faujasite or zeolite L has already been described (European Patent Specification 112,722, European Patent Specification 118,851 and Stud. Surf. Sci. Catal. (Amsterdam) 28 (1986) 747-754), only slightly higher selectivities have been stated for parachlorination, compared with ortho-chlorination. However, no dihalogenation of polynuclear aromatics in the presence of zeolites has yet been published, because a prejudice has obviously had to be overcome: on the one hand the shift mentioned in the ortho-para ratio is only slight if zeolites are used instead of conventional chlorination catalysts (FeCl$_3$/sulphur compounds); on the other hand, in view of the increased number of possible substitution patterns in polynuclear aromatics, an insignificantly pronounced selectivity and a multi-substance reaction mixture which is difficult to work up were to be expected.

Because of the particularly pronounced sparingly soluble nature of terphenyls dihalogenated in the 4,4"-position, of the formula

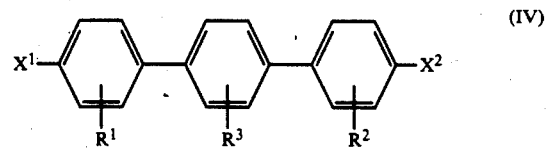

(IV)

in which
X$^1$, X$^2$, R$^1$, R$^2$ and R$^3$ have the abovementioned meaning, the process according to the invention is of particular importance for preparation of these compounds, terphenyls of the formula

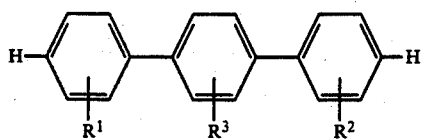

(V)

in which

R¹, R² and R³ have the abovementioned meaning, being used as starting substances.

This process is carried out in the manner described using halogenating agents in the presence of zeolites of the L structure type containing metal cations and furthermore in the presence of methylene chloride or mixtures essentially containing methylene chloride, in the stated amounts and at the stated temperatures, the reaction mixture formed, which contains the zeolite as a disperse solid phase and the 4,4″-dihalogeno-terphenyl as another solid phase, being extracted to obtain the 4,4″-dihalogeno-terphenyl.

EXAMPLES

All the zeolites mentioned in the following examples were calcined at 400° C. in a muffle furnace for 2 to 3 hours before being used.

Example 1

231.3 g (1.5 mol) of biphenyl and 1,000 ml of methylene chloride were brought together in a glass reactor with a ground glass flange (height 28 cm, diameter 11 cm) equipped with a stirrer, thermometer, reflux condenser and a gas inlet tube extending down to the bottom, and 45 g of pulverulent K zeolite L were added. A total of 234.3 g (3.3 mol) of $Cl_2$ gas were then passed into the suspension at 40° C. in the course of 6 hours, while stirring. After about half the time, a dense colourless precipitate started to separate out, which represented another solid disperse phase in addition to the zeolite. After 90% (191.7 g), 100% (213 g) and 110% (234.3 g) of the theoretically required amount of $Cl_2$ had been passed in, samples were taken to determine the conversion. As the following Table 1 shows (data in area % of the gas chromatography determination), the conversion is in each case 100%, based on the biphenyl employed. The selectivity for 4,4′-dichloro-biphenyl reaches a value of about 96% at 110% of the theoretical amount of $Cl_2$, without biphenyls which are more than dichlorinated being formed.

TABLE 1

| Sample with | Biphenyl | Monochloro-biphenyl | | Dichloro-biphenyl | | Remainder |
| --- | --- | --- | --- | --- | --- | --- |
| | | 2- | 4- | 2,4′- | 4,4′- | |
| 90% of $Cl_2$ | — | 2.33 | 34.95 | 1.35 | 60.77 | 0.60 |
| 100% of $Cl_2$ | — | 2.26 | 16.09 | 1.83 | 78.92 | 0.88 |
| 110% of $Cl_2$ | — | — | 0.25 | 3.56 | 95.54 | 0.65 |

Examples 2 to 13

35.5 g (0.5 mol) of $Cl_2$, were passed, in the course of 6-9 hours at the stated reaction temperature, into a suspension of 38.6 g (0.25 mol) of biphenyl and 7.5 g of zeolite powder of the type stated in 80 ml of $CH_2Cl_2$ in a 250 ml three-necked flask with a stirrer, thermometer, gas inlet tube and reflux condenser. After an after-stirring time of about 15 minutes, the composition of the reaction mixture was determined by gas chromatography (Table 2).

TABLE 2

| Example | Temperature | Zeolite | Biphenyl | Monochloro-biphenyl | | Dichloro-biphenyl | | Remainder | Total 4-/4,4′- |
| --- | --- | --- | --- | --- | --- | --- | --- | --- | --- |
| | | | | 2- | 4- | 2,4′- | 4,4′- | | |
| 2 | 20° C. | K-Ω | — | 27.52 | 3.38 | 20.85 | 38.01 | 10.24 | 41.39 |
| 3a | 20° C. | H-mordenite | — | 12.41 | 12.28 | 16.18 | 55.27 | 3.86 | 67.55 |
| 3b | 40° C. | H-mordenite | — | 9.57 | 16.14 | 13.78 | 56.15 | 4.36 | 72.29 |
| 4 | 40° C. | Rb—Y | — | 32.28 | 20.61 | 12.06 | 25.46 | 9.59 | 46.07 |
| 5 | 20° C. | H—L | 0.46 | 23.59 | 2.33 | 25.01 | 38.66 | 9.95 | 40.99 |
| 6 | 40° C. | $NH_4$—L | 0.12 | 19.58 | 30.92 | 8.46 | 35.02 | 5.9 | 65.94 |
| 7 | 20° C. | Na—L | 0.50 | 2.87 | 42.37 | 1.48 | 52.06 | 0.72 | 94.43 |
| 8 | 20° C. | K—L | — | 2.54 | 3.92 | 4.87 | 88.01 | 0.66 | 91.93 |
| 9 | 40° C. | Rb—L | 0.05 | 2.15 | 22.72 | 1.65 | 72.37 | 1.06 | 95.09 |
| 10 | 40° C. | Ba-l | 0.34 | 4.05 | 17.10 | 2.89 | 74.79 | 0.83 | 91.89 |
| 11 | 40° C. | La—L | — | 5.52 | 20.85 | 3.74 | 69.15 | 0.74 | 90.0 |
| 12 | 40° C. | Ag—L | 0.12 | 2.71 | 32.29 | 1.72 | 62.70 | 0.46 | 94.99 |
| 13 | 40° C. | Pb—L | 0.04 | 2.43 | 8.03 | 2.58 | 86.15 | 0.77 | 94.18 |
| 14 | 40° C. | none | 38.35 | 11.44 | 35.07 | 0.66 | 1.75 | 14.28 | 36.82 |

However, 4-monochloro-biphenyl present in the reaction mixture can be converted into 4,4,′-dichlorobiphenyl by further chlorination. The sum of 4-mono- and 4,4′-dichloro-biphenyl has therefore been stated in the last column of Table 2 in order to evaluate the 4,4′-selectivity.

Example 14

Table 2 contains Example 14, which was carried out without a zeolite catalyst and under otherwise identical reaction conditions.

Example 15

Example 8 was repeated, but the amount of zeolite K-L was halved (for the results see Table 3).

TABLE 3

| Example | Temperature | Zeolite | Amount of catalyst | Solvent | Biphenyl | Monochloro-biphenyl | | Dichloro-biphenyl | | Remainder | Total 4-/4,4′- |
| --- | --- | --- | --- | --- | --- | --- | --- | --- | --- | --- | --- |
| | | | | | | 2- | 4- | 2,4′- | 4,4′- | | |
| 15 | 20° C. | K—L | 10% | $CH_2Cl_2$ | 0.22 | 3.47 | 9.29 | 3.52 | 82.29 | 1.21 | 91.58 |
| 16 | 20° C. | K—L | 20% | $CHCl_3$ | 0.3 | 19.02 | 30.74 | 8.51 | 32.25 | 9.18 | 62.99 |
| 17 | 60° C. | K—L | 20% | $CHCl_3$ | — | 9.63 | 26.60 | 4.39 | 57.83 | 1.55 | 84.43 |
| 18 | 20° C. | K—L | 20% | $CCl_4$ | — | 12.58 | 7.33 | 13.49 | 60.85 | 5.75 | 68.18 |
| 19 | 40° C. | K—L | 20% | n-hexane | 9.71 | 11.59 | 54.72 | 2.22 | 18.99 | 2.77 | 73.71 |

TABLE 3-continued

| Example | Temperature | Zeolite | Amount of catalyst | Solvent | Biphenyl | Monochlorobiphenyl 2- | Monochlorobiphenyl 4- | Dichlorobiphenyl 2,4'- | Dichlorobiphenyl 4,4'- | Remainder | Total 4-/4,4'- |
|---|---|---|---|---|---|---|---|---|---|---|---|
| 20 | 20° C. | K—L | 20% | cyclohexane | 0.03 | 8.06 | 5.34 | 13.84 | 67.84 | 4.89 | 73.18 |
| 21 | 20° C. | K—L | 20% | 1,2-dichloropropane | 0.69 | 11.42 | 40.72 | 4.63 | 33.89 | 8.65 | 74.61 |
| 22 | 20° C. | K—L | 20% | 1,1,1-trichloroethane | 29.84 | 11.67 | 37.75 | 0.82 | 2.25 | 17.67 | 40.0 |

Examples 16 to 22 (for comparison)

Comparison examples were carried out in accordance with Example 8, but in these other solvents were employed instead of $CH_2Cl_2$.

Example 23

196 g (2.75 mol) of $Cl_2$ were passed into a suspension of 288 g (1.25 mol) of p-terphenyl and 58 g of K zeolite L powder in 2,500 ml of methylene chloride in the course of 10 hours. During this procedure, the non-zeolitic solid gradually dissolved and reprecipitated. After an after-stirring time of 15 minutes while passing through $N_2$, the reaction mixture showed the following composition, according to analysis by gas chromatography:
1.4% of 4-monochloro-terphenyl
1.9% of 2,4"-dichloro-terphenyl and
95.7% of 4,4"-dichloro-terphenyl, as well as 1% of unknown components.

The $CH_2Cl_2$, containing only small amounts of dissolved material from the reaction mixture, was filtered off and used in this form for another batch. The 4,4"-dichloro-terphenyl was isolated in a purity of 99.6–100% (from various batches) by recrystallization from o-dichlorobenzene. In the course of the recrystallization, the zeolite catalyst was obtained by filtration and washed with methylene chloride and could be used in this form in the next batch without a loss of activity.

Examples 24 and 25

17.8 g (0.25 mol) of $Cl_2$ were passed, at 40° C. in the course of 5 hours, into a suspension of 28.8 g (0.125 mol) of p-terphenyl and 5.75 g of zeolite powder of the type stated in 250 ml of $CH_2Cl_2$ in a 500 ml three-necked flask with a stirrer, gas inlet tube, thermometer and reflux condenser. The results of the analysis of the reaction mixture by gas chromatography and the nature of the zeolite are listed in Table 4.

Examples 26 to 32

The experiment was carried out as in Examples 24–15, the catalyst used being K-L (in Example 31 without a catalyst for comparison), the solvent used being $CHCl_3$, $CCl_4$ and $CH_2Cl_2$ or mixtures thereof, and a $Cl_2$ excess of up to about 100% of the theoretical amount being used. Three samples for analysis by gas chromatography were taken per experimental example, starting at the introduction of a $Cl_2$ excess of 10%. Further details can be seen from Table 4.

TABLE 4

(Data in area % of the gas chromatography analysis)

| Example | $Cl_2$ excess | Temperature | Zeolite | Solvent | Terphenyl | Mono-Cl-terphenyl n.d. | Mono-Cl-terphenyl n.d. | Mono-Cl-terphenyl 4- | Di-Cl-terphenyl 2,4"- | Di-Cl-terphenyl 4,4"- | Remainder | 4-/4,4"- Total |
|---|---|---|---|---|---|---|---|---|---|---|---|---|
| 24 | 0% | 40° C. | Pb—L | $CH_2Cl_2$ | 2.01 | 0.22 | 0.96 | 56.22 | 2.78 | 37.35 | 0.46 | 93.87 |
| 25 | 0% | 40° C. | Rb—L | $CH_2Cl_2$ | 1.24 | 0.05 | 0.52 | 52.21 | 1.84 | 40.61 | 3.53 | 92.82 |
| 26a | 10% | 60° C. | K—L | $CHCl_3$ | 29.95 | 2.82 | — | 52.77 | 1.13 | 10.33 | 3.0 | 63.1 |
| 26b | 88% | | | | 11.45 | 3.64 | — | 58.27 | 2.92 | 19.01 | 4.71 | 77.28 |
| 26c | 150% | | | | 1.69 | 2.80 | — | 52.40 | 5.11 | 32.37 | 5.63 | 84.77 |
| 27a | 10% | 75° C. | K—L | $CCl_4$ | 0.50 | 1.21 | — | 22.98 | 19.98 | 46.37 | 8.96 | 69.35 |
| 27b | 43% | | | | 0.09 | 0.01 | 8.62 | 4.39 | 22.63 | 50.97 | 13.29 | 55.36 |
| 27c | 69% | | | | — | — | 4.69 | 4.86 | 22.84 | 49.74 | 17.87 | 54.60 |
| 28a | 10% | 40° C. | K—L | $CH_2Cl_2$/ | 13.29 | 1.27 | — | 63.0 | — | 19.84 | 2.60 | 82.84 |
| 28b | 56% | | | $CHCl_3$ | 1.72 | 1.52 | — | 58.22 | 3.27 | 33.09 | 2.18 | 91.31 |
| 28c | 117% | | | 50:50 | 0.33 | 1.49 | — | 45.04 | 4.30 | 45.65 | 3.19 | 90.69 |
| 29a | 10% | 40° C. | K—L | $CH_2Cl_2$/ | 0.26 | — | — | 32.18 | 3.63 | 62.82 | 1.11 | 95.00 |
| 29b | 63% | | | $CHCl_3$ | — | — | — | 4.96 | 4.48 | 89.56 | 1.0 | 94.52 |
| 29c | 101% | | | 90:10 | — | — | — | 1.59 | 4.17 | 93.55 | 0.69 | 95.14 |
| 30a | 10% | 40° C. | K—L | $CH_2Cl_2$/ | — | — | — | 21.94 | 4.48 | 71.70 | 1.88 | 93.64 |
| 30b | 63% | | | $CHCl_3$ | — | 0.02 | — | 7.46 | 4.11 | 87.25 | 1.16 | 94.71 |
| 30c | 101% | | | 95:5 | — | — | — | 1.24 | 2.87 | 94.80 | 1.09 | 96.04 |
| 31a | 10% | 40° C. | none | $CH_2Cl_2$ | 45.63 | 8.73 | — | 32.69 | — | 4.16 | 8.79 | 36.85 |
| 31b | 63% | | | | 27.51 | 10.38 | — | 43.00 | — | 7.58 | 11.53 | 50.58 |
| 31c | 114% | | | | 13.72 | 11.28 | — | 48.32 | — | 11.93 | 14.75 | 60.25 |
| 32a | 10% | 40° C. | K—L | $CH_2Cl_2$ | — | — | — | 34.04 | 2.60 | 62.77 | 0.59 | 96.81 |
| 32b | 63% | | | | — | — | — | 1.65 | 2.48 | 94.68 | 1.19 | 96.33 |
| 32c | 101% | | | | — | — | — | 1.06 | 1.51 | 95.62 | 1.81 | 96.68 |

Examples 33 and 34 (for comparison)

77.1 g (0.5 mol) of biphenyl were melted in a stirred apparatus, while stirring and passing through nitrogen, 2 g of $FeCl_3$ were added and 71 g (1 mol) of $Cl_2$ gas were passed in at 100° C. in the course of 5 hours. The melt was kept at 100° C. for a further 30 minutes and degassed with nitrogen and its composition was determined by gas chromatography.

In another experiment (Example 34), 2 g of FeCl$_3$ and 2 g of thiophene were employed.

Examples 35–37 demonstrate the use of granulated or else bound zeolite L.

In a performance as in example 1 K-zeolite was replaced by granulates made of L-powder with binding agents wherein the content of pure zeolite L is indicated:

Example 35: 52.9 g K-L granulate with 15% SiO$_2$;

example 36: same as in example 35, but the granulate being pulverulized in a mortar before use;

example 37: 64.3 g K/Na-L granulate with 30% Al$_2$O$_3$.

The results of the gaschromatographic analysis are summarized in table 6.

TABLE 5

| | Product composition | | | | | | | | |
|---|---|---|---|---|---|---|---|---|---|
| | Monochloro-biphenyl | | Dichlorobiphenyls | | | | | Trichloro- | Remainder |
| Example | 2- | 4- | 2,2'- | 2,3'- | 2,4'- | 3,4'- | 4,4'- | * biphenyl* | (partly unknown) |
| 33 | 18.9 | 7.89 | 11.7 | 5.73 | 20.97 | 2.24 | 8.04 | 4.66 4.63 | 15.3 |
| 34 | 22.8 | 10.51 | 11.1 | 5.48 | 21.34 | 2.41 | 8.61 | 4.87 3.19 | 9.7 |

*unknown site of substitution

TABLE 6

| | | | Product composition (according to gas chromatography plane %) | | | | |
|---|---|---|---|---|---|---|---|
| Ex-ample | Cl$_2$ amount | Biphenyl | Monochloro-biphenyl | | Dichloro-biphenyl | | Re-mainder |
| | | | 2- | 4- | 2,4'- | 4,4'- | |
| 35 | 90 | — | 2.4 | 22.9 | 1.6 | 73.0 | 0.1 |
| | 100 | — | 2.1 | 4.5 | 2.2 | 91.0 | 0.2 |
| | 110 | — | 0.1 | — | 4.3 | 95.1 | 0.5 |
| 36 | 90 | 0.2 | 3.0 | 36.3 | 1.4 | 58.7 | 0.4 |
| | 100 | — | 3.1 | 19.6 | 2.1 | 74.7 | 0.5 |
| | 110 | — | 1.9 | 1.5 | 3.1 | 93.1 | 0.4 |
| 37 | 90 | 0.1 | 4.3 | 32.5 | 2.7 | 60.1 | 0.3 |
| | 100 | — | 3.9 | 14.0 | 3.6 | 78.1 | 0.4 |
| | 110 | — | 0.9 | 0.4 | 7.2 | 91.0 | 0.5 |

What is claimed is:

1. A process for the preparation of oligophenyls dihalogenated in the 4,4'-position, of the formula

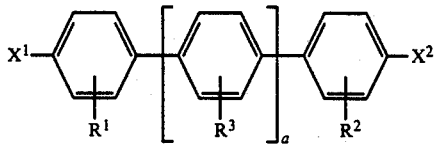

by halogenation of oligophenyls of the formula

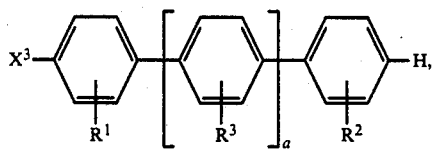

wherein, in the formulae,

X$^1$ and X$^2$ independently of one another represent chlorine or bromine,

X$^3$ denotes hydrogen, chlorine or bromine,

R$^1$, R$^2$ and R$^3$ independently of one another represent hydrogen, C$_1$–C$_4$-alkyl, C$_1$–C$_4$-alkoxy, fluorine, chlorine or bromine and a assumes the value zero or one, with halogenating agents selected from the group consisting of chlorine, bromine, and compounds which liberate chlorine or bromine, including sulphuryl chloride, sulphuryl bromide, N-chloro- and N-bromosuccinimide, bromine chloride and bromine fluoride, wherein the process is carried out at a temperature of from about 0°–80° C., in the presence of methylene chloride or solvent mixtures essentially containing methylene chloride and in the presence of zeolites of the L structure type containing metal cations.

2. The process of claim 1, wherein the halogenation is a chlorination.

3. The process of claim 1, wherein 60–100 equivalent % of all the cations are metal cations.

4. The process of claim 3, wherein 80–100 equivalent % of all the cations are metal cations.

5. The process of claim 4, wherein 90–100 equivalent % of all the cations are metal cations.

6. The process of claim 1, wherein the metal cations are those of Li, Na, K, Rb, Cs, Ca, Mg, Sr or Ba, of rare earth metals or Fe, Zn, Mn, Cr. Co, Ni, Ti, Cu, Ag or Pb, or mixtures of these.

7. The process of claim 1, which is carried out at 0°–80° C. The process of claim 1, which is carried out at 10°–45° C.

8. The process of claim 1, which is carried out in a reaction system in which, in addition to the methylene chloride as the liquid phase and the zeolite as a disperse solid phase, the oligophenyl or the 4,4'-dihalogeno-oligophenyl or both is (are) present as a further disperse solid phase.

9. The process of claim 8, wherein the reaction mixture in which the zeolite catalyst and the 4,4'-dihalogeno-oligophenyl are present as a disperse solid phase is worked up by extraction of the 4,4'-dihalogeno-oligophenyl.

10. A process according to claim 1, wherein the halogenating agent is selected from the group consisting of elemental chlorine or elemental bromine.

11. A process for the preparation of terphenyls dihalogenated in the 4,4''-position, of the formula

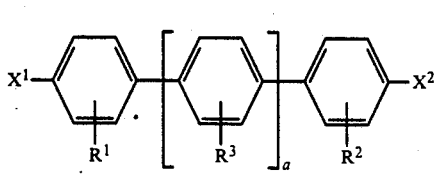

by halogenation of terphenyls of the formula

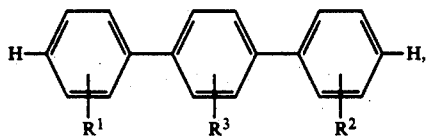

wherein, in the formulae
$X^1$ and $X^2$ independently of one another represent chlorine or bromine, and
$R^1$, $R^2$ and $R^3$ independently of one another represent hydrogen, $C_1$-$C_4$-alkyl, $C_1$-$C_4$-alkoxy, fluorine, chlorine or bromine, with halogenating agents selected from the group consisting of chlorine, bromine, and compounds which liberate chlorine or bromine, including sulphuryl chloride, sulphuryl bromide, N-chloro- and N-bromosuccinimide, bromine chloride and bromine fluoride, wherein the process is carried out at a temperature of from about 0°-80° C., in the presence of methylene chloride or mixtures essentially containing methylene chloride and in the presence of zeolites of the L structure type containing metal cations, and the reaction mixture formed, containing the zeolite as a disperse solid phase and the 4,4''-dihalogeno-terphenyl as another solid phase, is extracted to obtain the 4,4''-dihalogeno-terphenyl.

12. The process of claim 1, wherein $X^3$ denotes hydrogen or chlorine.

13. The process of claim 12, wherein $X^3$ denotes hydrogen.

14. The process of claim 1, wherein the halogenating agent is employed in a molar ratio of 2:1 to the oligophenyl in the case that $X^3$ denotes hydrogen, and in a molar ratio of 1:1 in the case that $X^3$ denotes chlorine or bromine, whereby this ratio can be deviated from upwards by up to 60 mol % to downwards by up to 20 mol %.

15. The process of claim 6, wherein the metal cations are those of K, Rb, Cs, Ca, sr, Ba, Ag, Pb or La or mixtures of these.

16. The process of claim 1, wherein the amount of methylene chloride employed is 0.3-100 times the weight of oligophenyl employed.

17. The process of claim 1, wherein in a solvent mixture essentially containing methylene chloride the methylene chloride is present in an amount of 50-100% by weight.

18. A process according to claim 11, wherein the halogenating agent is selected from the group consisting of elemental chlorine or elemental bromine.

* * * * *

UNITED STATES PATENT AND TRADEMARK OFFICE
CERTIFICATE OF CORRECTION

PATENT NO. : 5,053,566

DATED : October 1, 1991

INVENTOR(S) : Botta et al.

It is certified that error appears in the above-identified patent and that said Letters Patent is hereby corrected as shown below:

Title Page, item [56] U.S. PATENT DOCUMENTS: After " 4,950,817, 8/1990, Botta " insert -- et al. --

Col. 12, lines 41-42    Delete " The process of claim 1, which is carried out at 0°-80°C. "

Col. 12, line 64    Delete " 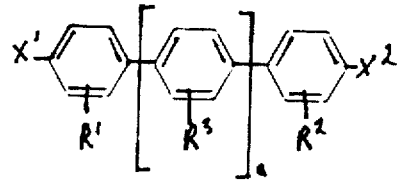 " and substitute

UNITED STATES PATENT AND TRADEMARK OFFICE
CERTIFICATE OF CORRECTION

PATENT NO. : 5,053,566

DATED : October 1, 1991

INVENTOR(S) : Botta, et. al.

It is certified that error appears in the above-identified patent and that said Letters Patent is hereby corrected as shown below:

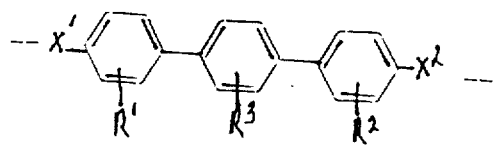

Col. 14, line 15    Delete " sr " and substitute -- Sr --

Signed and Sealed this

Twenty-fifth Day of May, 1993

Attest:

MICHAEL K. KIRK

Attesting Officer   Acting Commissioner of Patents and Trademarks